US00PP31110P2

(12) United States Plant Patent
Sills et al.

(10) Patent No.: US PP31,110 P2
(45) Date of Patent: Nov. 26, 2019

(54) BLACKBERRY PLANT VARIETY NAMED 'DRISBLACKEIGHTEEN'

(50) Latin Name: ***Rubus* L. subgenus *Rubus***
Varietal Denomination: DrisBlackEighteen

(71) Applicant: Driscoll's, Inc., Watsonville, CA (US)

(72) Inventors: Gavin R. Sills, Gilroy, CA (US); Pedro Jimenez, Watsonville, CA (US); Mark F. Crusha, Capitola, CA (US); Andrea M. Pabon, Gilroy, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/998,320

(22) Filed: Aug. 3, 2018

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| 2016/0249505 | P1 | 8/2016 | Sills et al. |

OTHER PUBLICATIONS

Sills et al., Unpublished U.S. Appl. No. 15/932,943, filed May 24, 2018, titled "Blackberry Plant Variety Named 'DrisBlackSeventeen'".
Voss, Donald H. "The Royal Horticultural Society Colour Chart 2001", Journal American Rhododendron Society, vol. 56, No. 1, 2002, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of blackberry plant named 'DrisBlackEighteen', particularly characterized by plant health, fruit size, lack of spines, and productivity, is disclosed.

4 Drawing Sheets

Latin name:
Botanical classification: *Rubus* L. subgenus *Rubus*.
Varietal denomination: The varietal denomination of the claimed variety of blackberry plant is 'DrisBlackEighteen'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed by the University of Arkansas capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackEighteen'.

Blackberry plant variety 'DrisBlackEighteen' was selected in Santa Cruz County, Calif. in June of 2007 and originated from a cross between the proprietary female parent blackberry plant 'DrisBlackTwo' (U.S. Plant Pat. No. 22,002) and the proprietary male parent blackberry plant 'BH936.7' (unpatented). The original seedling of the new variety was first asexually propagated via root cuttings in Santa Cruz County, Calif. in October of 2007.

'DrisBlackEighteen' was subsequently asexually propagated via root cuttings, and underwent, testing at a farm in Santa Cruz County, Calif. for 11 years. The present variety has been found to be stable and reproduce true to type through successive asexual propagations via root cuttings.

'DrisBlackEighteen' exhibits the following distinguishing characteristics over other similar varieties when grown under normal horticultural practices in Santa Cruz County, Calif.:

1. Larger, firmer fruit;
2. Earlier production; and
3. Earlier break in dormancy.

'DrisBlackEighteen' was selected for its plant health, fruit size, lack of spines, and productivity.

BRIEF DESCRIPTION OF THE DRAWINGS

This new blackberry plant is illustrated by the accompanying photographs, which show fruit of the plant, flowers, a leaf, and a plant. The colors shown are as true as can be reasonably obtained by conventional photographic procedures. The photographs are of plants that are three years old.

DETAILED BOTANICAL DESCRIPTION

Figure 1:
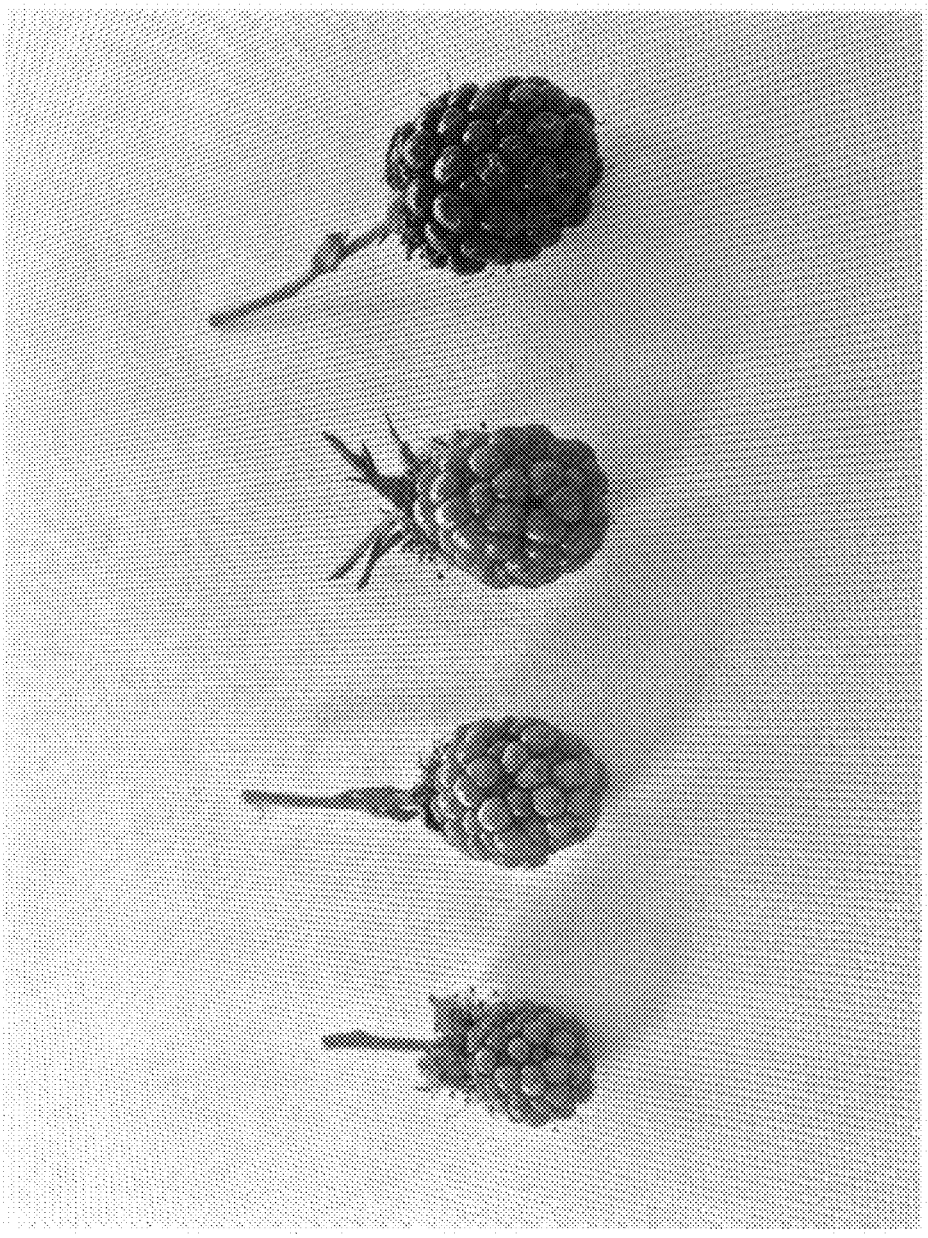
FIG. 1 illustrates typical fruit of variety 'DrisBlackEighteen' at various stages of development.
Figure 2:
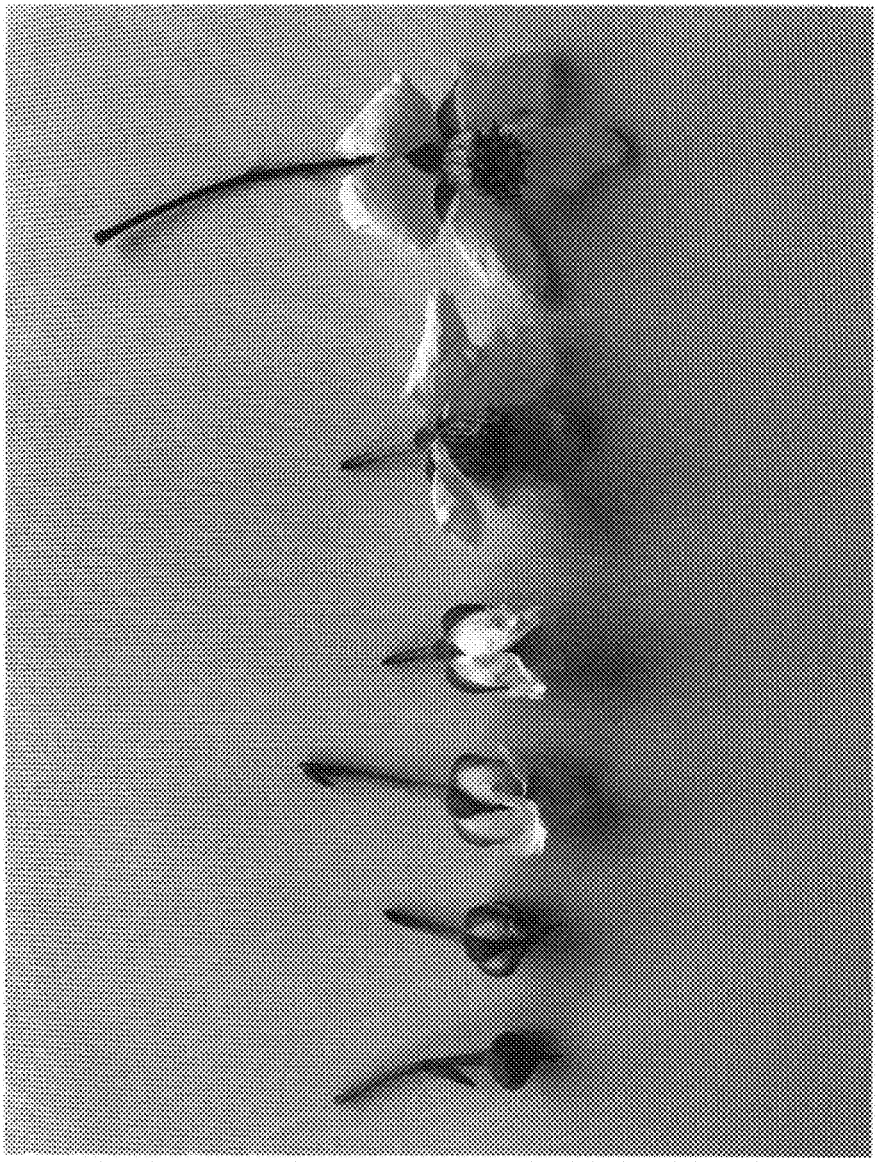
FIG. 2 illustrates typical flowers of variety 'DrisBlackEighteen' at various stages of development.
Figure 3:
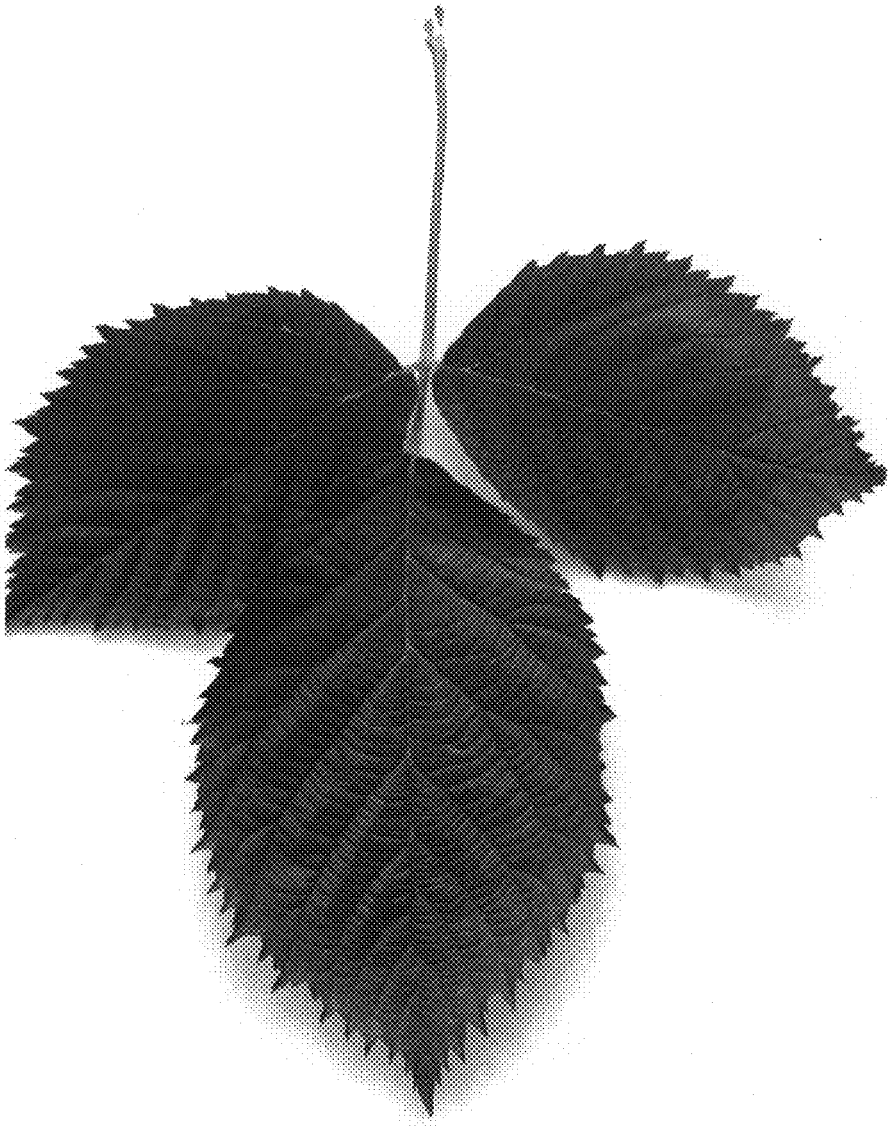
FIG. 3 illustrates a typical leaf of variety 'DrisBlackEighteen'.
Figure 4:
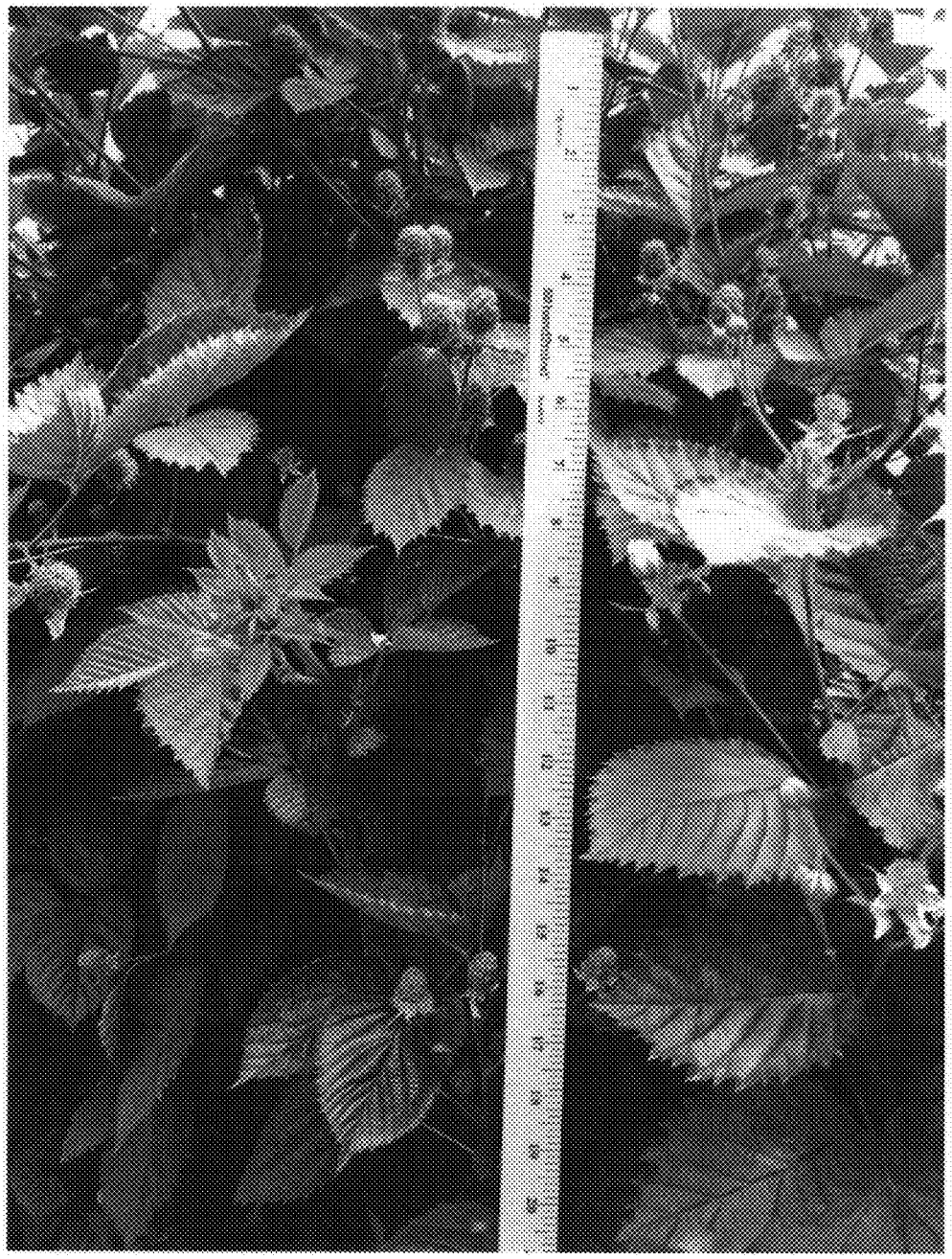
FIG. 4 illustrates a plant of variety 'DrisBlackEighteen'.

The following descriptions set forth the distinctive characteristics of 'DrisBlackEighteen'. The data that define these characteristics are based on observations taken in Santa Cruz County, Calif. for 11 years. This description is in accordance with UPOV terminology. Color designations, color descriptions, and other phenotypical descriptions may deviate from the stated values and descriptions depending upon variation in environmental, seasonal, climatic and cultural conditions. 'DrisBlackEighteen' has not been observed under all possible environmental conditions. The botanical description of 'DrisBlackEighteen' was taken from plants that were three years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackEighteen'.

Parentage:

*Female parent*.—'DrisBlackTwo' (U.S. Plant Pat. No. 22,002).

*Male parent*.—'BH936.7' (unpatented).

Plant:

*Propagation*.—Root cuttings.

*Growth habit*.—Upright to semi-upright.

*Plant height*.—221 cm.

*Plant width*.—76 cm.

Canes:

*Fruiting lateral length* (4$^{th}$ *lateral from tip*).—54.7 cm.

*Number of fruits per fruiting lateral*.—12.

*Internodal distance*.—7.6 cm.

*Dormant cane*.—Anthocyanin coloration: RHS 147A (Moderate olive green). Predominant distribution of branches: Over whole length. Cross-section: Angular. Presence of spines: Absent. Dormant cane diameter: 1.4 cm. Dormant cane texture: Smooth. Dormant cane intensity of green color: RHS 137A (Moderate olive green).

Young shoots:

*Anthocyanin coloration* (*during rapid growth*).—RHS 181A (Moderate red).

*Intensity of green color*.—RHS 147B (Moderate yellow-green).

*Young shoot length*.—26 cm.

*Young shoot diameter*.—1.2 cm.

*Young shoot texture*.—Smooth.

Leaves:

*Terminal leaflet*.—Length: 111.7 mm. Width: 91.0 mm. Length/width ratio: 1.2. Lobing: Absent. Shape in cross-section: V-shaped. Undulation of margin: Weak.

*Lateral leaflets* (*basal pair*).—Length: 94.2 mm. Width: 65.8 mm. Length/width ratio: 1.4.

*Rachis length between terminal leaflet and adjacent lateral leaflets*.—39.2 mm.

*Petiole*.—Length: 6.4 mm. Diameter: 2.1 mm.

*Leaflet*.—Type of incision of margin: Bi-serrate. Leaflet shape: Oblong to oval. Leaflet texture: Smooth to hairy. Leaflet color of lower side: RHS 138B (Moderate yellow-green).

*Leaf*.—Predominant number of leaflets: 5 for primocane leaves; 3 for floricane leaves. Type: Palmate.

Intensity of green color of upper side: RHS 147A (Moderate olive green). Leaf arrangement: Alternate. Leaf venation pattern: Fan. Leaf vein color: RHS 148D (Greyish yellow-green).

*Stipule*.—Stipule length: 1.6 cm. Stipule width: 0.3 cm. Stipule texture: Smooth. Stipule color: RHS 143B (Strong yellow-green).

Flowers:

*Diameter*.—53.70 mm.

*Petal*.—Length: 30.00 mm. Width: 15.50 mm. Length/width ratio: 1.9. Petal texture: Silky smooth. Petal margin: Smooth. Petal color of upper side: RHS 155A (Pale yellow-green). Petal color of lower side: RHS 155A (Pale yellow-green).

*Number of flowers observed at 3rd node from tip of lateral*.—3.

*Number of flowers per panicle*.—7.

*Presence of flower fragrance*.—Absent.

*Pedicel*.—Length: 58.20 mm. Diameter: 1.76 mm.

*Sepal*.—Sepal length: 1.4 cm. Sepal width: 0.6 cm. Sepal texture: Hairy. Sepal color: RHS 138C (Moderate yellow-green).

*Stigma*.—Stigma length: 0.25 mm. Stigma width: 0.25 mm. Stigma shape: Bottle cap-shaped. Stigma color: RHS 145C (Light yellow-green).

*Style*.—Style length: 4 mm. Style width: 0.25 mm. Style shape: Straw-shaped. Style color: RHS 146C (Moderate yellow-green).

*Ovary*.—Ovary length: 1 mm. Ovary width: 0.75 mm. Ovary shape: Seed-shaped. Ovary color: RHS 143B (Strong yellow-green).

*Stamen*.—Stamen length: 10 mm. Stamen width: 0.25 mm. Stamen shape: Tube-shaped. Stamen color: RHS 150D (Light yellow-green).

*Anther*.—Anther length: 0.25 mm. Anther width: 0.25 mm. Anther shape: Grain-shaped. Anther color: RHS 150D (Light yellow-green).

*Pollen*.—Pollen diameter: 0.001 mm. Pollen shape: Spherical. Pollen color: RHS 4D (Pale yellow-green).

*Peduncle*.—Peduncle diameter: 30 mm. Peduncle color: RHS 144A (Strong yellow-green).

*Flower bud*.—Date of bud burst: February 1. Bud length: 7 mm. Bud width: 5 mm. Bud shape: Spire-shaped. Bud color: RHS 148B (Moderate yellow-green).

*Time of beginning of flowering*.—Early May.

*Duration of flowering*.—6-8 weeks.

Fruit:

*Length of mature fruit*.—24.31 mm.

*Diameter of mature fruit*.—19.30 mm.

*Ratio of length to width*.—1.3.

*Shape in longitudinal section*.—Elliptic.

*Color*.—RHS 203A (Black).

*Fruiting on current year's cane*.—Absent.

*Yield*.—11,239 kg/acre to 13,854 kg/acre of fruit per season from 48-month-old plants when grown in Santa Cruz County, Calif.

*Druplet*.—Druplet diameter: 2 mm. Number of druplets per fruit: 94.

*Seed*.—Seed length: 2 mm. Seed width: 1 mm. Seed texture: Rough. Seed color: RHS 156A (Yellowish grey).

*Fruit weight*.—5.6 grams.

*Date of first fruit pick*.—February 1.

*Date of last fruit pick*.—August 5.

*Market use of fruit*.—Fresh consumption.

*Shipping and storage characteristics*.—Following harvest, fruit can be stored/shipped for 7 days under cooled temperatures standard for blackberry storage.

Resistance to diseases, pests, and abiotic stress:

*Redberry mite* (*Acalitus essigi*).—Susceptible.

*Powdery mildew* (*Podosphaera macularis*).—Moderately resistant.

*Fusarium wilt* (*Fusarium oxysporum*).—Resistant.

*Verticillium wilt* (*Verticillium spp.*).—Susceptible.

*Winter hardiness*.—Moderate.

*Drought tolerance*.—Moderate.

*Heat tolerance*.—Moderate.

COMPARISONS TO PARENTAL AND COMMERCIAL BLACKBERRY VARIETIES

'DrisBlackEighteen' differs from the proprietary female parent 'DrisBlackTwo' (U.S. Plant Pat. No. 22,002) in that fruit of 'DrisBlackEighteen' are larger in size and are more firm than fruit of 'DrisBlackTwo'. Moreover, fruit production of 'DrisBlackEighteen' is earlier than that of 'DrisBlackTwo'.

'DrisBlackEighteen' differs from the proprietary male parent 'BH936.7' (unpatented) in that fruit of 'DrisBlackEighteen' are larger in size and are more firm than fruit of 'BH936.7'. Moreover, 'DrisBlackEighteen' breaks dormancy earlier as compared to 'BH936.7'.

'DrisBlackEighteen' differs from commercial variety 'DrisBlackSix' (U.S. Plant Pat. No. 25,502) in that 'DrisBlackEighteen' has an upright to semi-upright growth habit, an angular cross section of dormant cane, a V-shaped terminal leaflet in cross-section, and an elliptic fruit shape in longitudinal section. In contrast, 'DrisBlackSix' has a semi-upright growth habit, a rounded to angular cross section of dormant cane, a U-shaped terminal leaflet in cross-section, and a narrow ovate fruit shape in longitudinal section.

'DrisBlackEighteen' differs from commercial variety 'Driscoll Carmel' (U.S. Plant Pat. No. 15,058) in that 'DrisBlackEighteen' has an upright to semi-upright growth habit, no spines on dormant canes, and an elliptic fruit shape in longitudinal section. In contrast, 'Driscoll Carmel' has a semi-upright growth habit, spines present on dormant canes, and an ovate fruit shape in longitudinal section.

What is claimed is:

1. A new and distinct variety of blackberry plant designated 'DrisBlackEighteen' as shown and described herein.

* * * * *